United States Patent

Perry et al.

[11] Patent Number: 4,830,017
[45] Date of Patent: May 16, 1989

[54] AUTOMATIC POSITIONING SYSTEM FOR CONTINUOUS BLOOD PRESSURE MONITOR TRANSDUCER

[75] Inventors: William D. Perry; Dean C. Winter, both of San Antonio, Tex.

[73] Assignee: Nippon Colin Co., Ltd., Komaki, Japan

[21] Appl. No.: 160,140

[22] Filed: Feb. 25, 1988

[51] Int. Cl.$^4$ .............................. A61B 5/02
[52] U.S. Cl. ...................... 128/672; 128/677; 128/687
[58] Field of Search ............... 128/672, 690

[56] References Cited

U.S. PATENT DOCUMENTS

| | | | |
|---|---|---|---|
| 3,123,068 | 3/1964 | Bigliano | 128/672 |
| 3,219,035 | 11/1965 | Pressman et al. | 128/672 |
| 3,585,987 | 6/1971 | Svensson | 128/672 |
| 3,880,145 | 4/1975 | Blick | 128/672 |
| 4,206,765 | 6/1980 | Huber | 128/677 |
| 4,307,727 | 12/1981 | Haynes | 128/672 |
| 4,423,738 | 1/1984 | Newgard | 128/675 |

Primary Examiner—Kyle L. Howell
Assistant Examiner—Angela D. Sykes
Attorney, Agent, or Firm—Matthews & Branscomb

[57] ABSTRACT

A system for automatically positioning a blood pressure monitor transducer in a desired position relative to an underlying artery. The positioning system comprises a positioniong motor which drives a gear assembly. The gear assembly is operatively engaged with a lead screw having a follower mounted thereto in threaded engagement therewith. The follower is secured to a strap which is routed through a roller system. As the motor is activated in response to output signals from the sensor mounted within transducer housing, the lead screw will rotate, thereby effectuating lateral movement of the transducer housing and sensor along a path defined by the strap.

6 Claims, 6 Drawing Sheets

AUTOMATIC POSITIONING SYSTEM FOR CONTINUOUS BLOOD PRESSURE MONITOR TRANSDUCER

FIELD OF THE INVENTION

The present invention relates generally to a method and apparatus for continuous noninvasive measurement of blood pressure. More specifically, the present invention provides a method and apparatus for maintaining a continuous blood pressure monitor transducer properly positioned over an underlying artery in order to ensure that at least one of the pressure sensing elements in the transducer tracks the actual pulse waveform in the underlying artery, thus providing the most accurate measurement of the patient's blood pressure.

BACKGROUND

There has been considerable interest in recent years in the development of a monitoring system for obtaining a continuous measurement of a patient's blood pressure. One of the most promising techniques for obtaining such a continuous measurement involves the use of an arterial tonometer comprising an array of small pressure sensing elements fabricated in a silicon "chip." The use of such an array of sensor elements for blood pressure measurements is disclosed generally in the following U.S. Patents.: U.S. Pat. Nos. 3,123,068 to R. P. Bigliano, 3,219,035 to G. L. Pressman, P. M. Newgard and John J. Eige, 3,880,145 to E. F. Blick, 4,269,193 to Eckerle, and 4,423,738 to P. M. Newgard, and in an article by G. L. Pressman and P. M. Newgard entitled "A Transducer for the Continuous External Measurement of Arterial Blood Pressure" (IEEE Trans. Bio-Med. Elec., April 1963, pp. 77-81).

In a typical tonometric technique for monitoring blood pressure, a transducer which includes an array of pressure sensitive elements is positioned over a superficial artery, and a hold-down force is applied to the transducer so as to flatten the wall of the underlying artery without occluding the artery. The pressure sensitive elements in the array have at least one dimension smaller than the lumen of the underlying artery in which blood pressure is measured, and the transducer is positioned such that more than one of the individual pressure-sensitive elements is over at least a portion of the underlying artery. The output from one of the pressure sensitive elements is selected for monitoring blood pressure. The element that is substantially centered over the artery has a signal output that provides an accurate measure of intraarterial blood pressure. However, for the other transducer elements the signal outputs generally do not provide as accurate a measure of intraarterial blood pressure as the output from the centered element. Generally, the offset upon which systolic and diastolic pressures depend will not be measured accurately using transducer elements that are not centered over the artery. One method for selecting the pressure sensitive element for monitoring blood pressure is disclosed in the above mentioned U.S. Pat. No. 4,269,193 issued to J. S. Eckerle. In addition, an improved method for selecting the correct pressure sensitive element for measuring blood pressure is disclosed in a patent application entitled "Active Element Selection for Continuous Blood Pressure Monitor Transducer" filed on even date herewith.

One of the difficulties encountered in the development of tonometric blood pressure monitoring systems is the correct placement of the transducer on the patient's wrist such that the pressure sensing elements are centered over the underlying artery. The positioning system of the present invention, described in greater detail below, overcomes this difficulty.

SUMMARY OF THE INVENTION

The present invention provides an automatic positioning system for maintaining a continuous blood pressure monitor transducer properly positioned over an underlying artery in order to ensure that a plurality of the pressure sensing elements in the transducer track the actual pulse waveform in the underlying artery. In the preferred embodiment, the pulse amplitude output signals from each of the pressure sensing elements in the sensor array are monitored and used to generate a tonogram indicating the approximate position of the sensor relative to the underlying artery. When the sensor is properly centered over the artery, the tonogram will exhibit a characteristic peak which is usually near the center of the tonogram. However, when the transducer is offset to either side of the artery, the tonogram will be a curve having primarily either a positive or a negative slope without a clearly defined peak.

In the automatic positioning system of the present invention, the tonogram of the pulse amplitudes is used to determine the position of the transducer relative to the underlying artery and to maintain the transducer in the optimal position. The preferred embodiment of the positioning system comprises a gear motor which is operatively engaged with a lead screw/follower mechanism by means of a pair of gears. The gear motor effectuates rotation of the lead screw in response to appropriate signals indicating the position of the sensor relative to the underlying artery. Rotation of the lead screw causes the transducer housing to travel or move laterally along a path defined by a transducer strap. Lateral movement of the housing in response to the rotation of the lead screw is caused by the threaded engagement of the follower with the lead screw and the securement of the follower to the strap in a fixed position. The travel of the transducer housing is further facilitated by a roller mechanism through which the strap is routed. The movement of the housing, in response to feedback from the sensor, continues until the sensor is appropriately positioned over the underlying artery.

DETAILED DESCRIPTION OF THE PREFERRED EMBODIMENT

Figure 1:
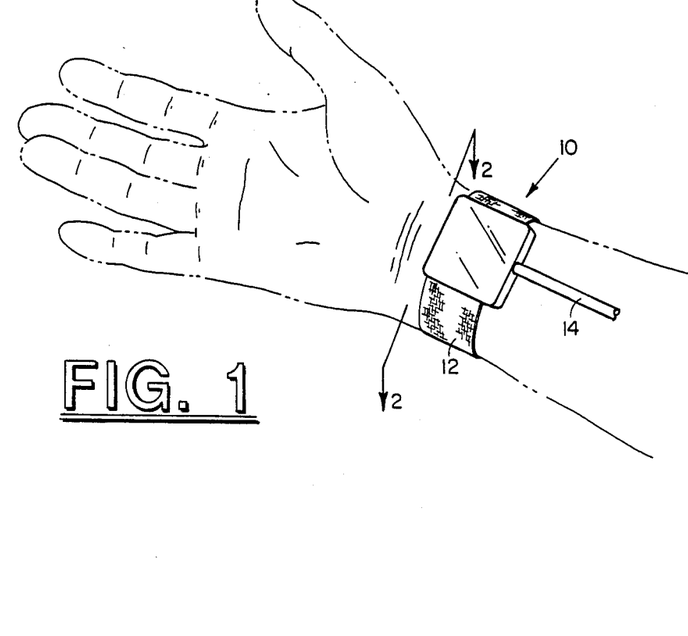
FIG. 1 is a view of the continuous blood pressure monitoring transducer of the present invention attached to a patient's wrist at a position overlying the radial artery.

Reference is now made to FIG. 1 wherein a continuous blood pressure monitor transducer 10 is shown attached to a patient's wrist at a point overlying the radial artery. The transducer is attached by means of a strap 12 in a manner similar to a conventional wristwatch. A cable assembly 14 connected to the transducer contains electrical cables for carrying electrical signals to and from the transducer. The cable assembly 14 also contains a pneumatic tube for providing pressurized air to a pressurizable bladder in the interior of the transducer in order to bring a sensor into contact with the patient's skin in a manner described in greater detail hereinbelow.

For the transducer to properly measure blood pressure it is important that the underlying artery be partially compressed. Specifically, it is important that the artery be flattened by a plane surface so that the stresses developed in the arterial wall perpendicular to the face of the sensor are negligible. This generally requires that the blood pressure measurement be taken on a superficial artery which runs over bone, against which the artery can be flattened.

Figure 2:
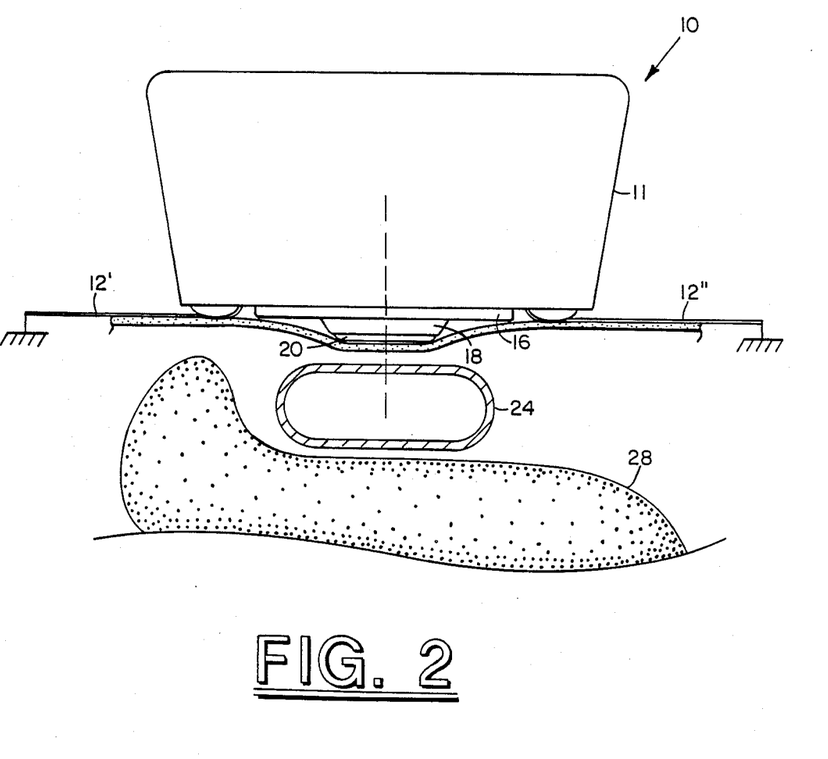
FIG. 2 is a cross sectional side view taken along section lines 2—2 of FIG. 1 illustrating the continuous blood pressure monitor positioned over an artery with the artery being partially flattened in response to pressure applied by a transducer piston assembly.

FIG. 2 is a cross sectional side view, taken along section lines 2—2 of FIG. 1, showing the continuous blood pressure monitor positioned on the patient's wrist at a point overlying the radial artery 24. A transducer piston 16 including a sensor mounting platform 18 is shown protruding from the bottom of the transducer to flatten the artery 24 against the radius bone 28. A sensor 20 is mounted on the lower surface of the sensor mounting platform 18. The sensor 20 comprises a plurality of pressure sensing elements described below. In FIG. 2, the ends 12' and 12'' of the strap 12 are shown attached to ground symbols to illustrate that the strap is firmly secured to the patient's wrist. In practice, the strap is secured in generally the same manner as that for a conventional wrist watch.

Figure 3:
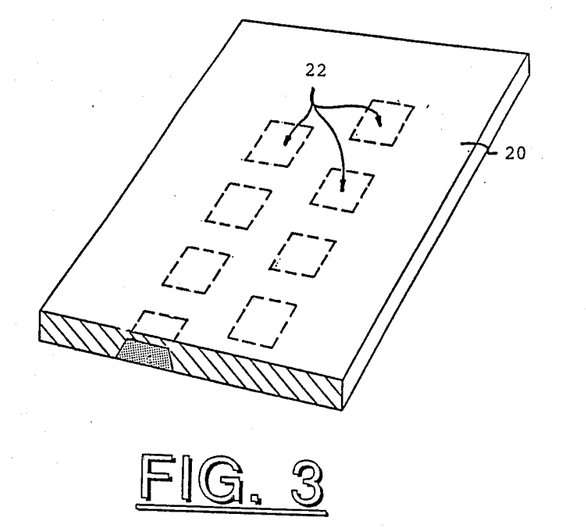
FIG. 3 is a perspective view of an array of pressure sensing elements, etched in a monocrystaline silicon substrate, of the type employed in the pressure transducer of the present invention.

FIG. 3 is a perspective view of the sensor 20 used in the continuous blood pressure monitor of the preferred embodiment. The sensor 20 comprises an array of individual pressure sensing elements 22 which are formed in a thin rectangular monocrystalline silicon substrate using conventional but modern integrated circuit techniques. One method which can be used to form such a silicon chip with regions of predetermined thickness in the chip is described in U.S. Pat. No. 3,888,708 issued to Wise, et al. for "Method for Forming Regions of Predetermined Thickness in Silicon." In the sensor shown in FIG. 3, the individual pressure sensing elements 22 are shown aligned in two rows. This particular arrangement is shown only for purposes of illustration. In practice, various numbers of force sensitive elements can be used, depending on the desired monitoring resolution, and various patterns can be used for arranging the sensing elements within the silicon substrate.

Figure 4:
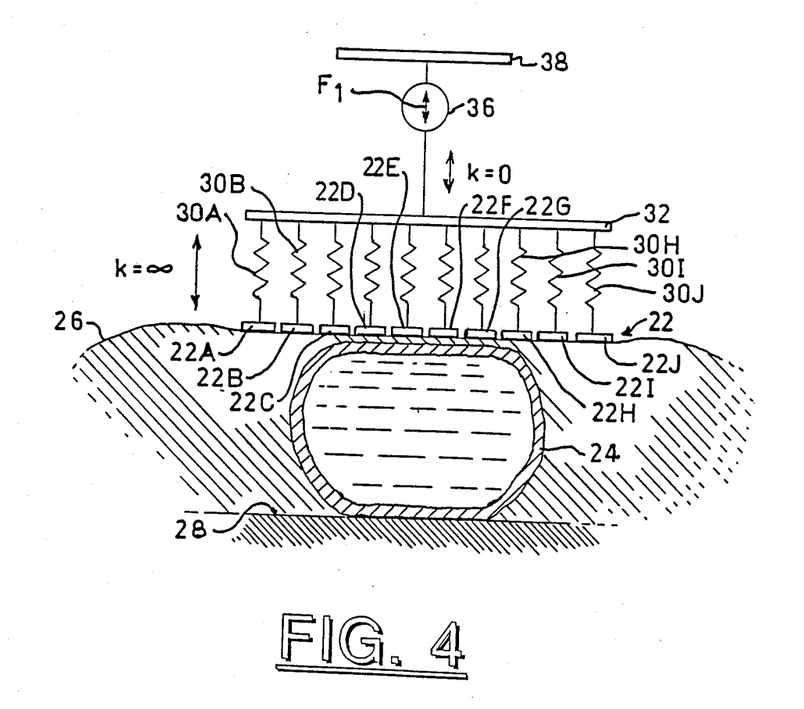
FIG. 4 is a schematic diagram illustrating the force balance between the artery and the multiple transducer elements (arterial riders), with the artery wall properly depressed to give accurate blood pressure readings.

Reference now is made to FIG. 4 wherein a diagrammatic mechanical model is shown which is representative of physical factors to be considered in blood pressure measurements using tonometry techniques. The illustrated model is adapted from that shown in the above-mentioned U.S. Pat. No. 4,269,193, issued to J. S. Eckerle, which by this reference is incorporated for all purposes. An array 22 of individual pressure sensitive elements or transducers 22-A through 22-E, which constitute the arterial riders, is positioned so that one or more of the riders are entirely over an artery 24. The individual riders 22-A through 22-E are small relative to the diameter of the artery 24, thus assuring that a plurality of the riders overlie the artery. The skin surface 26 and artery underlying the transducer must be flattened by application of a hold-down pressure to the transducer. One rider overlying the center of the artery is identified as the "centered" rider, from which rider pressure readings for monitoring blood pressure are obtained. Means for selecting the centered rider are discussed general in the above mentioned U.S. Pat. No. 4,269,193. In addition, an improved means for selecting the best pressure sensing element for measuring blood pressure is disclosed in a patent application entitled "Active Element Selection for Continuous Blood Pressure Monitor Transducer" filed on even date herewith. For present purposes it will be understood that one of the riders, such as rider 22-E, may be selected as the "centered" rider, in which case the remainder of the riders, here riders 22-A through 22-D and 22-F through 22-J, comprise "side plates" which serve to flatten the underlying skin and artery.

Superficial arteries, such as the radial artery, are supported from below by bone which, in FIG. 4, is illustrated by ground symbol 28 under the artery. The wall of artery 24 behaves substantially like a membrane in that it transmits tension forces but not bending moments. The artery wall responds to the loading force of the transducer array, and during blood pressure measurements acts as if it is resting on the firm base 28. With the illustrated system, the transducer assembly 10 and mounting strap 12, together with air pressure applied to a pressurizable bladder in the transducer assembly, supply the required compression force and hold the riders 22-A through 22-J in such a manner that arterial pressure changes are transferred to the riders which overlie the artery 24. This is illustrated schematically in FIG. 4 by showing the individual riders 22-A through 22-J backed by rider spring members 30-A through 30-J, respectively, a rigid spring backing plate 32, and holddown force generator 36 between the backing plate 32 and the mounting strap system 38.

If, without force generator 36, the coupling between the mounting strap system 38 and spring backing plate 32 were infinitely stiff to restrain the riders 22-A through 22-J rigidly with respect to the bone structure 28, the riders would be maintained in a fixed position relative to the artery. In practice, however, such a system is not practical, and hold-down force generator 36, comprising (in the present example) a pneumatic loading system, is included to keep constant the force applied by the mounting strap system 38 to riders 22-A through 22-J. In the mechanical model the spring constant, k (force per unit of deflection) of the force generator, 36, is nearly zero. Pneumatic loading systems are shown and described in the abovereferenced U.S. Pat. Nos. 3,219,035 and 4,269,193, and the Pressman and Newgard IEEE article. In addition, an improved pneumatic loading system is disclosed in a patent application entitled "Pressurization System for Continuous Blood Pressure Monitor Transducer" filed on even date herewith.

In order to insure that the riders 22-A through 22-J flatten the artery and provide a true blood pressure measurement, they must be rigidly mounted to the backing plate 32. Hence, the rider springs 30-A through 30-J of the device ideally are infinitely rigid (spring constant $k = \infty$). It is found that as long as the system operates in such a manner that it can be simulated by rider springs 30-A through 30-J having a spring constant on the order of about ten times the corresponding constant for the artery-skin system, so that the deflection of riders 22-A through 22-J is small, a true blood pressure measurement may be obtained when the correct hold-down pressure is employed.

Figure 5:
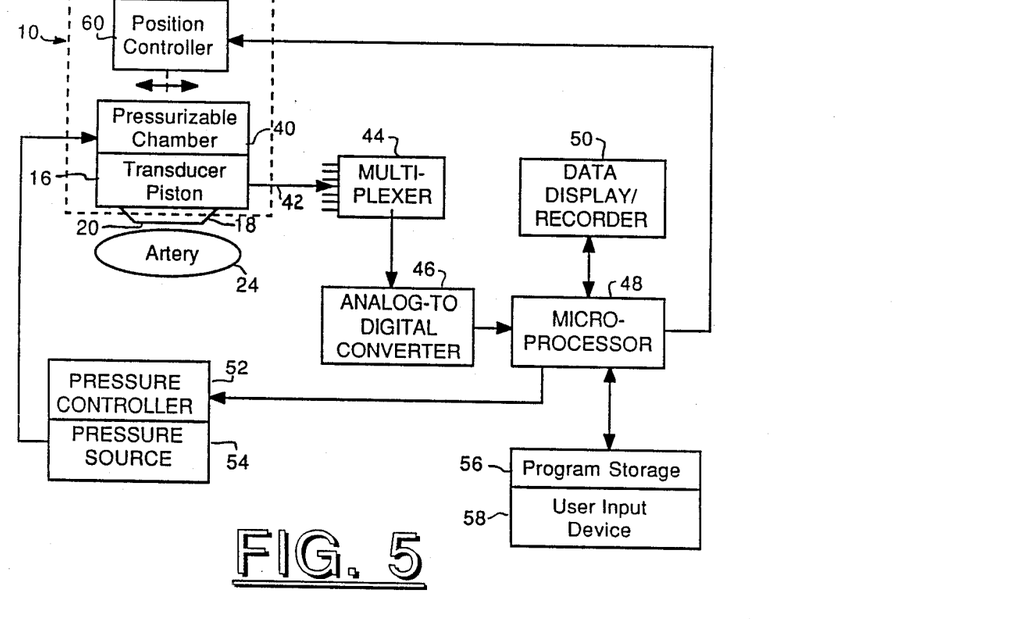
FIG. 5 is a simplified block diagram of the system components for monitoring a plurality of force sensing elements to generate a tonogram which can be used to control a positioning system to maintain the transducer assembly at a desired position over an underlying artery.
Figure 5A:
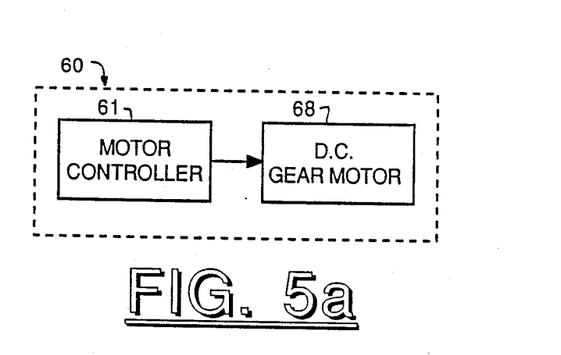
FIG. 5a is a block diagram of the position controller.

Referring to FIG. 5, a simplified illustration of the transducer assembly 10 is shown to include a transducer piston 16, a pressurizable chamber 40 and a position controller 60. In FIG. 5a, the position controller can be seen to comprise a motor controller 61 and a D.C. gear motor 68. The output of the individual pressure sensors (not shown) on the sensor 20 are connected by appropriate electrical wiring 42 to the input of a multiplexer 44. From the multiplexer, the signals are digitized by an analog-to-digital (A-D) converter 46, and the digitized signals are supplied to a microprocessor 48. Output from the microprocessor 48 is supplied to data display and recorder means 50 which may include a recorder, cathode ray tube monitor, a solid state display, or any other suitable display device. Also, the output from the microporcessor 48 is provided to the pressure controller 52 which controls a pressure source 54 to maintain the appropriate pressure in the pressurizable chamber 40, thus ensuring the proper hold down pressure for the transducer piston 16. Operation of the microprocessor 48 can be controlled by a program contained in program storage 56 or by user input from the user input device 58, which can be in the form of a keyboard or other interface device, such as a "joystick," etc. The program storage 56 or the user input device 58 can be used to cause the microprocessor 48 to control operation of the position controller 60 as described in greater detail below.

Figure 6:
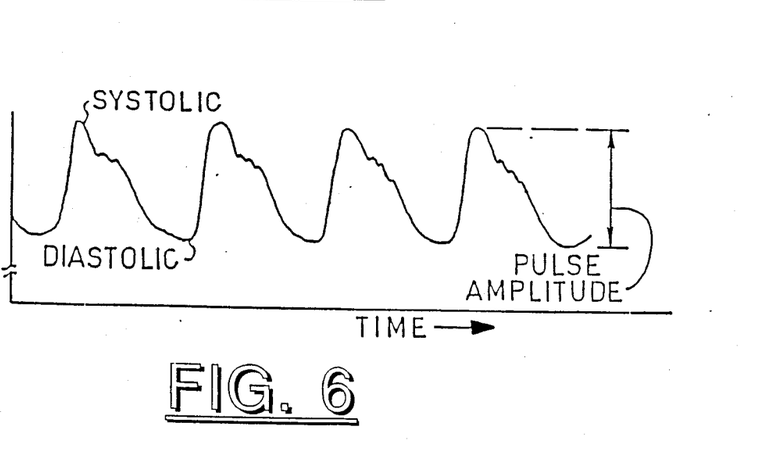
FIG. 6 is a waveform of human blood pressure versus time of the type which may be obtained using the present invention for illustrating systolic and diastolic pressures and pulse amplitude of the blood pressure wave.

Reference is now made to FIG. 6 which illustrates the signal waveform of the output from one of the pressure sensitive elements 22-A through 22-J which overlies artery 24. Other elements of the transducer array which overlie the artery will have waveforms of similar shape. With a correct hold-down pressure and correct selection of the "centered" arterial rider (i.e., the rider substantially centered over the artery) the waveform is representative of the blood pressure within the underlying artery. Systolic, diastolic and pulse amplitude pressures are indicated on the waveform, wherein pulse amplitude is the difference between the systolic and diastolic pressures for a given heartbeat.

Figure 7A:
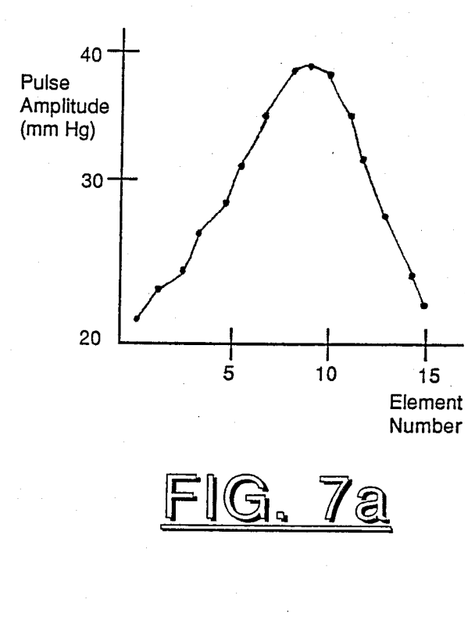
FIG. 7a is a graphical representation of a tonogram of pulse amplitudes measured by the force sensing elements of the continuous blood pressure monitor transducer when the transducer is properly positioned over the underlying artery.
Figure 7B:
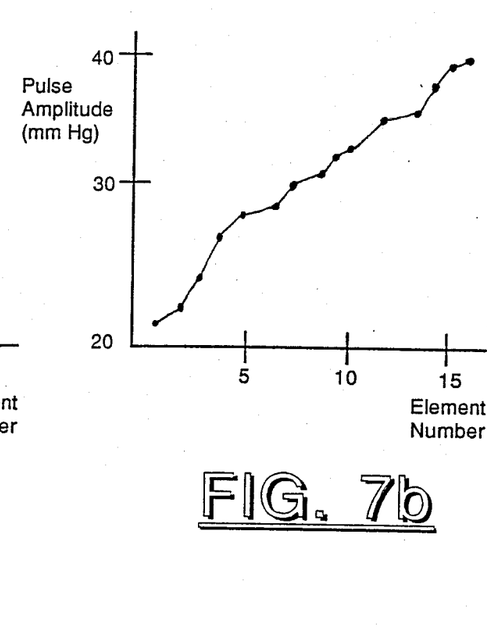
FIG. 7b is a graphical representation of a tonogram of pulse amplitudes measured by the force sensing elements of the continuous blood pressure monitor transducer when the transducer is improperly positioned over the underlying artery.
Figure 7C:
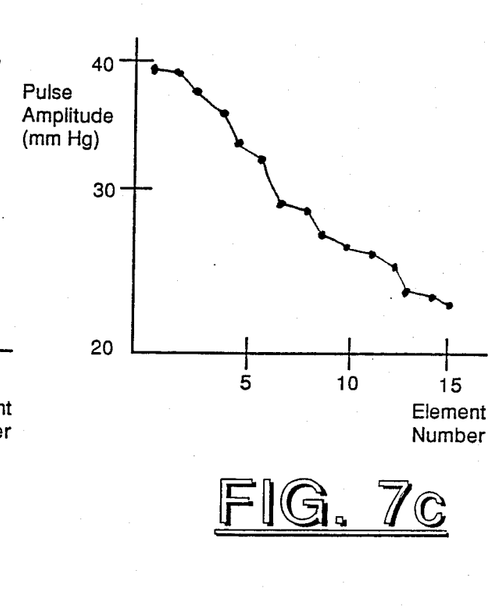
FIG. 7c is another graphical representation of a tonogram of pulse amplitudes measured by the force sensing elements of the continuous blood pressure monitor transducer when the transducer is improperly positioned over the underlying artery.

A graphical illustration, or "tonogram," of the pulse waveforms produced by the portion of the artery underlying the sensor 20 can be formed by displaying the respective pulse pressure output signals produced by each of the pressure sensing elements 22. The tonogram can then be used to determine whether the transducer assembly 10 is properly positioned over the artery. FIGS. 7a-7c illustrate tonograms for sensors which are properly centered over an artery, as well as for sensors which are offset to either side from the center of the artery. For the tonograms illustrated in FIGS. 7a-7c, pulse pressures have been illustrated for a sensor having 15 pressure sensing elements. It is to be understood that the element no. 1 would occupy the approximate position illustrated for element 22-A in the model shown in FIG. 4 and that element no. 15 would occupy the approximate position illustrated for element 22-J. FIG. 7a is a typical tonogram for a sensor which is properly centered over an underlying artery. The tonogram produced by the plurality of pressure sensing elements exhibits a peak at approximately the center of the tonogram. FIGS. 7b and 7c, however, illustrate tonograms which are produced by sensors which are offset either in direction A or direction B, as illustrated in FIG. 4, from the center of the underlying artery. FIG. 7b is a typical tonogram which is produced by a sensor which is offset in direction A shown in FIG. 4. FIG. 7c is a typical tonogram which is produced by a sensor which is offset in direction B shown in FIG. 4.

Figure 8:
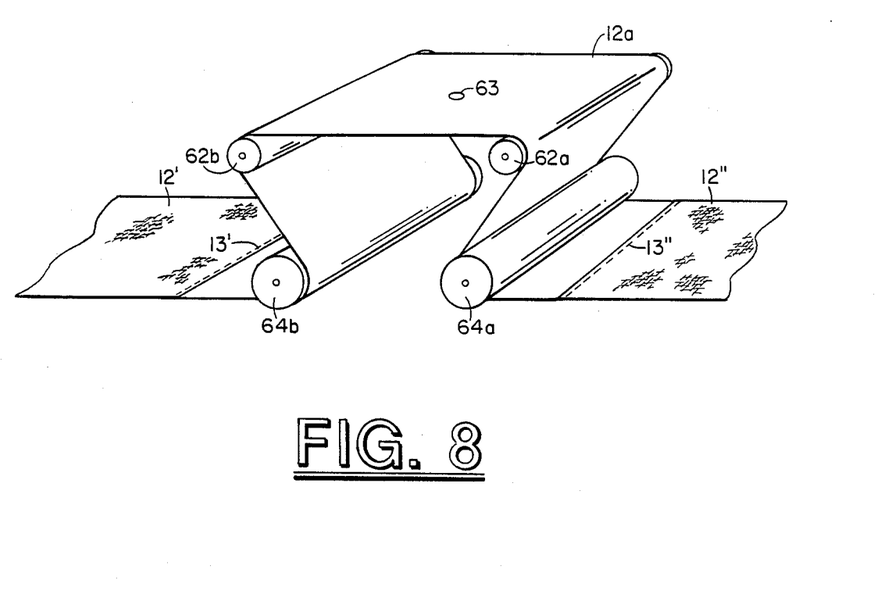
FIG. 8 is a perspective view of the transducer assembly of the present invention showing the routing of the transducer strap through the transducer roller system.
Figure 9A:
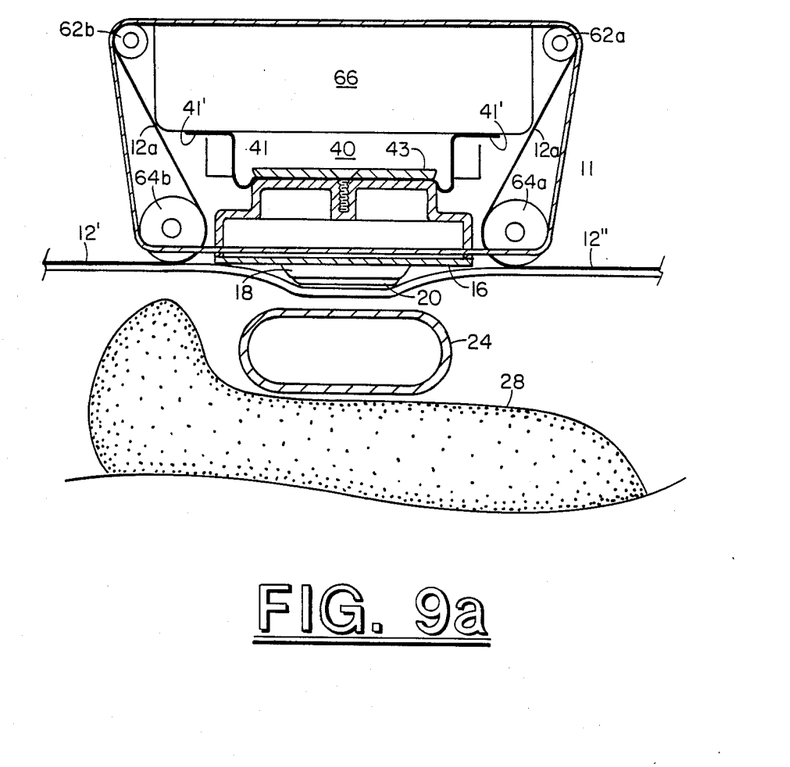
FIG. 9a is a cross-sectional side view showing the routing of the strap over a system of rollers used in the automatic positioning system of the preferred embodiment.
Figure 9B:
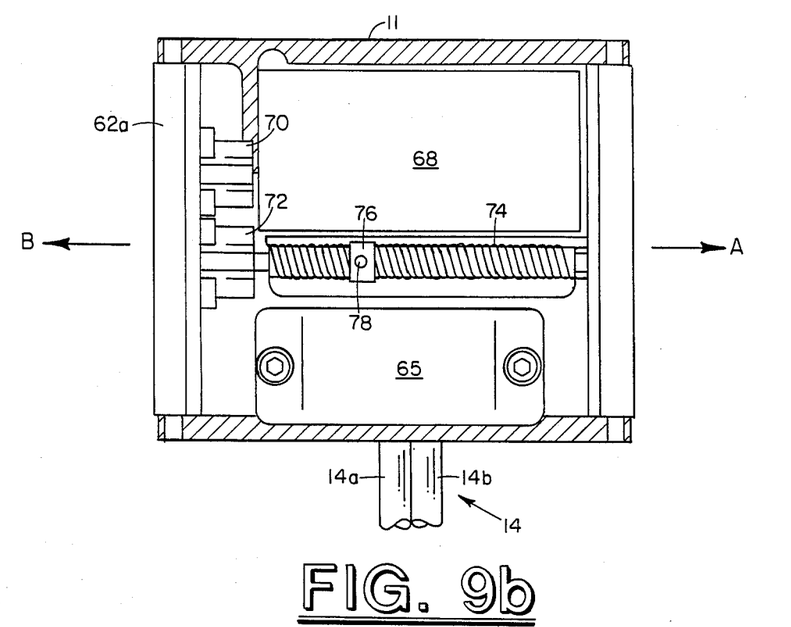
FIG. 9b is a top plan view of the transducer assembly of the preferred embodiment.
Figure 9C:
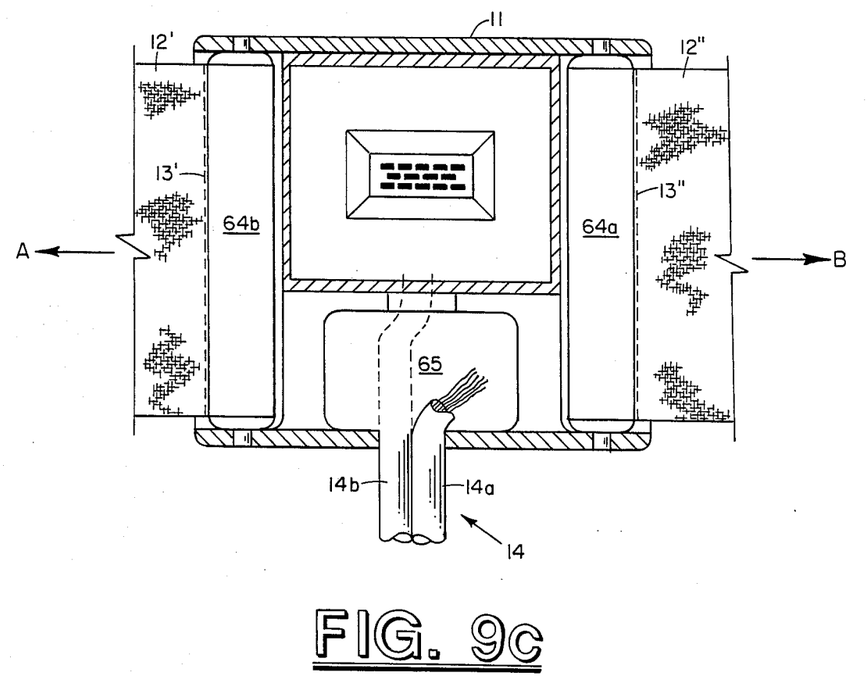
FIG. 9c is a bottom plan view of the transducer assembly of the preferred embodiment.

Referring to FIG. 8 and FIG. 9a, the positioning system of the present invention will be described in greater detail. The positioning system is utilized to correctly position the transducer assembly so that the sensor 20 is properly centered over an underlying artery. As illustrated in FIG. 8 and FIG. 9a, the strap 12 is routed around a roller system comprising upper rollers 62a and 62b and lower rollers 64a and 64b. Rollers 62a, 62b, 64a, and 64b are appropriately mounted to outer housing 11, as illustrated in FIG. 9b and FIG. 9c, so as to permit rotation of the rollers. The portion of the strap 12 which is in contact with the rollers is formed of a strip 12a of semirigid plastic which is attached to portions 12' and 12'' of the strap by stitched seams 13' and 13'', respectively, as shown in FIG. 8. An aperture 63 in the strap portion 12a is adapted to receive a connector screw 78 (illustrated in FIG. 9b) to secure the transducer assembly to the strap 12 as the outer housing 11 moves laterally along the path defined by strap portion 12a.

Referring to FIG. 9b and FIG. 9c, the apparatus for moving the housing 11 laterally along the path or track defined by strap portion 12a comprises a DC gear motor 68 which is operatively engaged with a first gear 70 so as to appropriately drive or rotate gear 70. Motor 68 is mounted within motor housing 66 (illustrated in FIG. 9a), which is mounted to and within outer housing 11. Gear 70 is appropriately engaged with a second gear 72 so as to effectuate rotation of gear 72 upon rotation of gear 70. A lead screw 74 is appropriately mounted to and within housing 11 and engaged with gear 72 so that rotation of gear 72 will effectuate rotation of lead screw 74. Lead screw 74 has a follower 76 mounted thereon in threaded engagement therewith. Follower 76 has an upstanding screw 78 connected thereto which extends through aperture 63 to secure follower 76 to strap 12.

Referring again to FIG. 9b and FIG. 9c, the operation of the positioning system will be described in greater detail. The gear motor 68 responds to output signals from the motor controller 61 so as to effectuate clockwise or counter clockwise rotation of gear 70, thereby effectuating rotation of gear 72 and lead screw 74. Due to the securement of follower 76 to strap portion 12a and the threaded engagement of follower 76 with lead screw 74, the rotation of lead screw 74 will cause housing 11 and sensor 20 to move laterally in direction A or B, depending upon the direction of rotation of lead screw 74. As the gear motor 76 appropriately activates or rotates lead screw 74 by means of gears 70 and 72, the sensor 20 is thereby accurately positioned and properly centered over an underlying artery.

Referring again to FIG. 9a, details relating to the pressurizable chamber 40 will be described in greater detail. A flexible silicon rubber bellows or diaphragm 41 is shown with its perimeter attached to the lower surface of the motor housing 66 and is further secured to the top of the sensor piston 16 by means of a plate 43. The sealed perimeter portion of the diaphragm is illustrated by reference number 41' in FIG. 9a. Both of the above mentioned attachments of the diaphragm 41 provide air tight seals. With the diaphragm 41 attached to the lower face of the motor housing 66 and the upper surface of the transducer piston assembly as described above, a pressurizable chamber 40 is formed within the transducer housing assembly. Since the flexible rubber bellows is sealed both to the transducer piston 16 and to the lower face of the motor housing 66, pressurized air introduced into the pressurizable cavity 40 causes the transducer piston 16 to be pneumatically loaded. As the pressure in the cavity 40 is increased the transducer piston assembly 16 will be forced downward to the position shown in FIG. 9a. Pressurized air is introduced by means of a pneumatic tube 14b which is in fluid communication with chamber 40 and may extend through terminator housing 65, as illustrated in FIG. 9c. The pneumatic pressure applied inside the rubber bellows 41 may be adjusted to supply the compressional force required to provide the necessary flattening of the artery wall, thus allowing the device to meet the flattening criteria described above in connection with FIG. 2. Furthermore, the pressure source of the present invention can be used to provide a constant pressure to maintain the artery in an optimally flattened condition. When the transducer case is held in place on the wrist, generally over the radial artery, as shown in FIG. 1, the transducer piston 16 is thus supported over the radial artery by the rubber bellows, air pressure inside the bellows holds the sensor 20 and its supporting structure, against the skin surface with sufficient force to achieve the desired degree of flattening of the wall of the artery. Therefore, the individual force sensing elements in the sensor will produce output signals which accurately track the pulse wave form in the underlying artery.

In operation, the positioning system of the present invention can be operated manually by a user who views the display 50 and inputs directional commands via the user input device, e.g., arrow keys on a computer keyboard, to cause the transducer to move in the desired direction. Alternatively, a program stored in program storage 56 can be used to cause the microprocessor to provide an appropriate control signal to the motor controller 61, thus moving the D.C. gear motor to cause repositioning of the transducer assembly. Such a program would include curve analysis techniques which are well known in the art and can be implemented by a programmer of ordinary skill.

Although the method and apparatus of the present invention has been described in connection with the preferred embodiment, it is not intended to be limited to the specific form set forth herein, but on the contrary, it is intended to cover alternatives and equivalents as may reasonable be included within the spirit and scope of the invention as defined by the appended claims.

I claim:

1. A system for maintaining a blood pressure monitor transducer properly positioned over an artery, comprising:
   a transducer housing;
   a sensor contained within said housing, said sensor comprising a plurality of pressure sensing elements, each of said elements producing an output signal proportional to the pulse amplitude in said underlying artery;
   processing means responsive to said sensor element output signals for forming an ordered relation between said output signals and for generating an output signal indicating the desired position of said sensor; and
   means for moving said housing in response to said output signal from said processing means.

2. The system according to claim 1, said ordered relation between said output signals from said elements being in the form of a tonogram.

3. The system according to claim 2, wherein said means for moving said housing comprises a housing drive assembly secured to said housing and a strap defining a path for housing travel.

4. The system according to claim 3, wherein said drive assembly comprises a d.c. gear motor and a motor controller.

5. The system according to claim 4, said strap being routed through a system of rollers in said housing.

6. The system according to claim 5, said strap comprising a portion formed from a semirigid plastic material.

* * * * *